United States Patent [19]
Lin

[11] Patent Number: 4,643,734
[45] Date of Patent: Feb. 17, 1987

[54] LACTIDE/CAPROLACTONE POLYMER, METHOD OF MAKING THE SAME, COMPOSITES THEREOF, AND PROSTHESES PRODUCED THEREFROM

[75] Inventor: Steve Lin, Dublin, Calif.

[73] Assignee: Hexcel Corporation, San Francisco, Calif.

[21] Appl. No.: 491,927

[22] Filed: May 5, 1983

[51] Int. Cl.⁴ .............................................. A61F 2/28
[52] U.S. Cl. .................................................... 623/16
[58] Field of Search ................... 528/354; 128/334 R, 128/92 C, 92 BC, 92 G; 260/78.3; 3/1, 1.9; 623/16, 17, 18, 19, 20, 21, 22, 23

[56] References Cited
U.S. PATENT DOCUMENTS

| | | |
|---|---|---|
| 4,045,418 | 8/1977 | Sinclair .............................. 260/78.3 |
| 4,057,537 | 11/1977 | Sinclair .............................. 260/78.3 |
| 4,243,775 | 1/1981 | Rosensaft .......................... 528/354 |
| 4,329,743 | 5/1982 | Alexander et al. ...................... 3/1 |
| 4,379,138 | 5/1983 | Pitt et al. ............................. 128/1 |
| 4,443,430 | 4/1984 | Mattei et al. ....................... 528/354 |

Primary Examiner—Richard J. Apley
Assistant Examiner—David J. Isabella
Attorney, Agent, or Firm—Oblon, Fisher, Spivak, McClelland & Maier

[57] ABSTRACT

A bio-absorbable copolymer of lactide and epsilon caprolactone comprising a major amount of epsilon caprolactone and a minor amount of lactide; a method of making the same; a composition of said polymer and at least one substrate of a plurality of carbon fibers; surgical articles of said composition; and a method of repairing ligaments and tendons are disclosed.

23 Claims, 2 Drawing Figures

LACTIDE/CAPROLACTONE POLYMER, METHOD OF MAKING THE SAME, COMPOSITES THEREOF, AND PROSTHESES PRODUCED THEREFROM

BACKGROUND OF THE INVENTION

1. Field of the Invention

This invention relates to lactide/caprolactone co-polymers, a method of making the same, composites of the same with carbon fibers, and prostheses produced from such composites.

2. Description of the Prior Art

The treatment of injured ligaments and tendons remains a serious clinical problem. Inadequately repaired damage to these structures results in pain, loss of function, and in some cases, subsequent degenerative arthritis. When severly damaged by trauma or disease, fibrous tissue repair is often impossible. Many researchers have suggested the use of replacement structures for such damaged tissue. At this time, however, a completely successful prosthesis for use in a chronic implantation has not been developed.

It has recently been demonstrated by Jenkins et al, "Induction of Tendon and Ligament Formation by Carbon Implants", *J. Bone and Joint Surg.*, 59-B:53-57, 1977, and Wolter et al, "Ligament Replacement in the Knee Joint with Carbon Fibers Coated with Pyrolytic Carbon", *Trans. 3rd Ann. Mtg., Soc. for Biomat.*, 126, 1977, that ligaments and tendons can be replaced by filamentous carbon implants. New fibrous tissue grows and is gradually aligned, replacing the carbon scaffold which fractures and degrades mechanically.

Alexander et al, "Carbon-Polymer Composites for Tendon and Ligament Replacement", *Trans. 4th Ann. Mtg., Soc. for Biomat.*, 123, 1978, have indicated the need for physically protecting the delicate carbon fibers to avoid difficulty in implantation, premature fracturing in vivo and migration of carbon fibers from the site of surgery.

Kulkarni et al, "Polylactic Acid for Surgical Implant", *Arch. Surg.*, 93, 839-843, 1966, and Cutright et al, "Tissue Reaction to the Biodegradable Polylactic Acid Suture", *Oral Surg.*, 31: 134-139, 1971, have demonstrated the biocompatibility, biodegradability and ease of manufacture of surgical appliances of polylactic acid polymers.

U.S. Pat. Nos. 4,127,902 and 3,971,670 describe structures for in vivo implantation as substitutes for ligaments and tendons comprising a bio-compatible film, a bio-compatible fabric having a weave with no permanent yield in one direction integral with the film and a bio-compatible porous material which promotes the ingrowth of living tissue. The structure is used as a patch for repairing damaged ligaments and tendons and is designed to promote the growth of new ligament and tendon tissue. The patch, however, is intended for permanent implantation in the host animal.

U.S. Pat. No. 3,276,448 discloses the concept of coating a non-absorbable fiber-containing fabric intended for use as a repair structure for damaged tissue with collagen. The collagen is said to serve as a stimulus for new tissue growth in the area of repair.

It has been proposed in U.S. Pat. No. 3,992,725 to utilize carbon fibers as in vivo implantation material due to its ability to foster new tissue growth by virtue of its bio-compatibility. The patent proposes to combine the carbon fibers with polytetrafluoroethylene bonding material to provide a relatively permanent implant material.

U.S. Pat. No. 3,463,158 discloses the use of composites of polyglycolic acid and non-absorbable fibrous material as implants for tissue repair or replacement. The composition is designed such that new tissue growth surrounds the non-absorbable fibrous material.

U.S. Pat. No. 3,893,196 describes a material for fabricating a prosthesis comprising graphite fibers embedded in a coating with a medically inert plastic.

U.S. Pat. No. 3,272,204 discloses an absorbable collagen prosthetic implant reinforced with strands of non-absorbable material.

U.S. Pat. Nos. 4,045,418 and 4,057,537 describe lactide/caprolactone polymers wherein the lactide is present in major amount. The polymers are taught to be bio-degradable. More particularly, U.S. Pat. No. 4,057,537 discloses copolymers of L-(−)-lactide and epsilon caprolactone wherein the concentration of L-(−)-lactide and epsilon caprilactone which is heated to form copolymers is in the range of about 50 to about 90 wt % based on the total mixture, preferably, about 75 to about 90 wt % (column 3, lines 10-48). Example 1 of this patent discloses the preparation of a 50/50 copolymer of L-(−)-lactide/epsilon caprolactone which is characterized as gummy and having a low tensile strength.

U.S. Pat. No. 3,268,487 discloses a process for the polymerization of lactides.

U.S. Pat. No. 3,531,561 discloses surgical sutures prepared by extruding high molecular weight polylactide polymers. Comonomers may be included in the polymer in minor amounts, e.g., 5–15% by weight.

U.S. Pat. No. 3,636,956 discloses absorbable surgical sutures prepared by the extrusion of polylactide polymers wherein the polymer may contain up to 35 mole % of a glycolide.

U.S. Pat. No. 3,839,297 discloses high molecular weight co-polymers of lactide and glycolactide which may be extruded to make absorbable surgical sutures.

U.S. Pat. No. 4,300,565 discloses sterile surgical articles fabricated from synthetic absorbable copolymers formed by co-polymerizing glycolide monomer with a cyclic ester monomer other than glycolide, lactide being preferred.

As is apparent from the aforesaid references, many absorbable polymers are known and the use of filamentous carbon as an implant material is not unique. Indeed, it has been demonstrated that new fibrous tissue growth is encouraged by the carbon filaments, with the new tissue gradually aligning and replacing the carbon scaffold which fractures and degrades mechanically. However, filamentous carbon is usually produced on a polymer base, often with the addition of polymer sizing agents. These polymers frequently exhibit adverse tissue reactions or are carcinogens; as is polyacrylonitrile, a commonly used base material. It has been suggested to remove the sizing agent with methyl ethyl ketone possibly leaving trace polymer material behind. Complete removal of the sizing and base residue by heating to 4000° F. results in a strong material that is, unfortunately, brittle and sensitive to shear and bending deformations.

In addition, unprotected carbon has been found to break up during implantation and migrate from its implantation area. In some cases, it forms sinus tracks right through the skin.

The mere mechanical reinforcement of the carbon fibers with other materials does not satisfactorily eliminate the migration problem.

Recently, in U.S. Pat. No. 4,329,743 for Bio-Absorbable Composite Tissue Scaffold, there has been disclosed a bio-compatible composition for fabricating a surgical article for the repair or replacement of a part of the body of a human or non-human animal comprising a composite of a bio-absorbable polymer and at least one substrate of a plurality of carbon fibers. Suitable bio-absorable polymers are polyglycolic acid, polylactic acid and collagen. By enveloping the carbon fiber substrate with a bio-absorbable polymer migration of the filamentous carbon after implantation is prevented, without interfering with the new tissue growth promoting characteristics of the carbon fiber substrate. The polymer functions as a mechanical reinforcer for the carbon fibers during tissue growth, and the polymer degrades allowing new tissue growth to replace it, thereby allowing a transference of load from the composite to the new tissue over an extended period of time.

However, the polylactic acid polymers disclosed therein are quite rigid and even when plasticized with, for example, polyethylene glycol, the coated carbon fiber tow is very rigid and the carbon fibers break when bent. Moreover, the plasticizer tends to decrease the adhesion between polymer and fibers.

A need therefore continues to exist for polymers and composites thereof which offer the advantages of polymer bio-absorbability, composite flexibility and good adhesion to the carbon fibers by the polymer without damage to the carbon fiber substrate.

SUMMARY OF THE INVENTION

Accordingly, one object of the invention is to provide a bio-absorbable polymer which when coated on a carbon fiber substrate affords a tough, flexible film, which protects the carbon fibers from breaking.

Another object of the invention is to provide a method of making a bio-absorbable polymer which affords a tough, flexible film when coated on a carbon fiber substrate.

Another object of the invention is to provide a bio-compatible composition suitable for constructing a surgical article for the repair or replacement of a part of the body of a human or non-human animal comprising a composite of a bio-absorbable polymer and at least one substrate of a plurality of carbon fibers.

Another object of the invention is to provide a bio-compatible surgical article suitable for incorporation in the body of a human or non-human animal for the repair or replacement of a part thereof wherein the article is constructed of the above-described composite composition.

Another object of the invention includes a method for the manufacture of a bio-compatible surgical article comprising: providing at least one substrate of a plurality of carbon fibers; coating said at least one substrate with a bio-absorbable polymer; and, shaping said at least one substrate into a surgical article of suitable shape and size.

A further object of this invention also includes a surgical method for the repair or replacement of a part of the body of a human or non-human animal by incorporating therein the above-described surgical article.

Briefly, these objects and other objects of the invention as hereinafter will become more readily apparent can be attained by providing a polymer of a lactide and epsilon caprolactone formed from a mixture of the monomers wherein the epsilon caprolactone is present in major amount.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
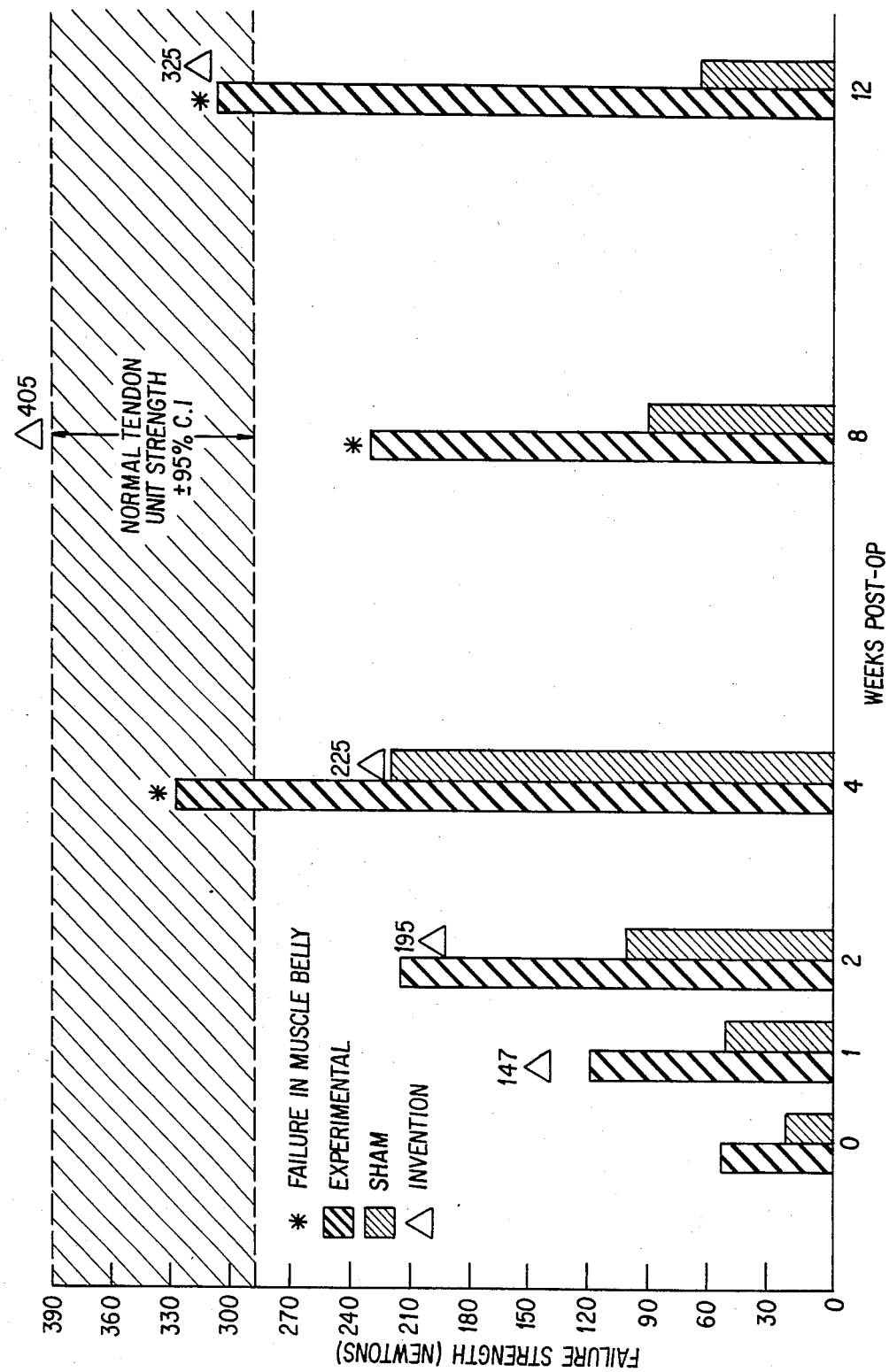
FIG. 1 is a graphical representation of the tensile strength of ligaments repaired using various procedures versus the time elapsed from the operative procedure.

The polymer of the present invention is a copolymer of a lactide and epsilon caprolactone. The proportions of lactide and epsilon caprolactone can vary over a considerable range, so long as the epsilon caprolactone is present in the mixture of lactide and epsilon caprolactone, which is reacted to form the copolymer, in major amount. Preferably, the concentration of epsilon caprolactone in the mixture of lactide and epsilon caprolactone which is reacted to form the copolymer is in the range of about 60 to about 95 weight percent, based on the total weight of the mixture. The concentration of lactide in the mixture of lactide and epsilon caprolactone which is reacted to form the copolymer is in the range of about 40 to 5 weight percent, based on the total weight of the mixture. Most preferably, a mixture of about 75 weight percent epsilon caprolactone and about 25 weight percent of lactide is used to prepare the desired copolymer which is tough, having excellent elongation, of high tensile strength, and of a weight average molecular weight of about 200,000–500,000.

The lactide of the present invention corresponds to the general formula (I)

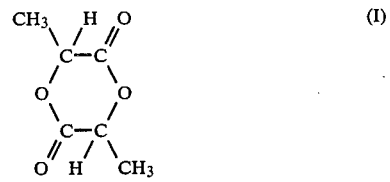

The lactide employed in accordance with the present invention can be optically active, e.g., L-(−)-lactide, or optically inactive, e.g., D,L-lactide. The L-(−)-lactide, which is a cyclic dimer of L-(+)-lactic acid, is commercially available. L-(−)-lactide is a white powder having a molecular weight of 144. If desired, commercially available L-(−)-lactide can be purified by recrystallization from anhydrous methyl isobutyl ketone, ethyl acetate or acetone. The snow-white crystals of L-(−)-lactide melt at about 95°–98° C. D,L-lactide is a cyclic dimer of D,L-lactic acid and is commercially available. D,L-lactide frequently comprises a mixture of D,D-, L,L- and D,L-lactide. Accordingly, when used herein, the term "D,L-lactide" is intended to include D,L-lactide and mixtures thereof with D,D- and/or L,L-lactide. D,L-lactide is a white powder having a molecular weight of 144. As with the L-(−)-lactide, commercially available D,L-lactide can be purified by conventional means, i.e. recrystallization from anhydrous methyl isobutyl ketone, ethyl acetate or acetone. The snow-white crystals obtainable melt at about 115°–129° C.

The epsilon caprolactone of the present invention corresponds to the general formula (II)

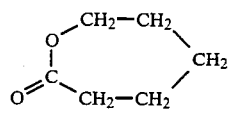

(II)

The epsilon caprolactone employed in accordance with the present invention is commercially available. Commercially available epsilon caprolactone can be purified by vacuum distillation, i.e. collecting that portion boiling at 56°–57° C./0.4 torr. Epsilon caprolactone is water-white with a single gas chromotography peak.

In preparing the lactide/epsilon caprolactone copolymer in accordance with this invention, it is preferred to carry out the reaction at atmospheric pressure in the liquid phase (either as a melt or in an inert liquid diluent) in the presence of a catalyst, blanketed by an inert gas such as, for example, nitrogen. The copolymers can also be prepared in a closed, evacuated vessel. If the polymerization is conducted in the presence of air, discoloration occurs along with a resulting degradation of polymer properties. The process can be carried out at any temperature above the melting point of the lactide, preferably, 10° C. above the lactide melting point. However, temperatures above 200° C. are undesirable because of the tendency of the copolymer to degrade. Temperatures below the melting point of the lactide can be used, if the reactants are dispersed or dissolved in an inert liquid, however, the use of lower temperatures prolongs the reaction and may result in less desirable polymers. Increasing the temperature of the reaction within the range from the melting point of the lactide to 200° C., generally increases the speed of the polymerization. Preferably, the mixture of lactide and epsilon caprolactone is reacted at a temperature of about 140°–150° C.

The catalysts employed in accordance with the present invention are metallic esters of carboxylic acids. Preferably, the carboxylic acid contains up to 18 carbon atoms. Examples of such acids are formic, acetic, propionic, butyric, valeric, caproic, caprylic (octoic), pelargonic, capric, lauric, myristic, palmitic, stearic, and benzoic acids. Preferred esters are the tin and zinc esters of carboxylic acids containing up to 18 carbon atoms. Good results have been obtained with stannous octoate and zinc octoate.

The catalyst concentration is preferably in the range of about 0.01 to about 1.0 percent by weight based on the total weight of the lactide and epsilon caprolactone. Good results have been obtained using catalyst concentration in the range of about 0.02 to about 0.03 percent by weight. The exact amount of catalyst in any particular case depends to a large extent upon the catalyst employed and the operating variables including time, temperature and pressure.

The reaction time, in most instances, is governed by the other reaction variables, e.g., temperature, pressure, catalyst, amount of catalyst, and whether a liquid vehicle is employed. In general, the reaction time will be in the range of hours to days, depending upon the particular set of conditions which are employed. For example, it takes at least 48 hours to complete a bulk polymerization reaction at atmospheric pressure and 140° C. when the catalyst concentration employed is about 0.02 percent by weight.

The polymerization is always carried out until no further reaction is detected which can be easily determined by monitoring the percent conversion of monomeric reactants versus reaction time, for example, using thermogravimetric analysis (TGA).

In general, it is preferred to conduct the polymerization in the absence of impurities which contain active hydrogen since the presence of such impurities tends to deactivate the catalyst and/or increase the induction time. It is also preferred to conduct the polymerization under substantially anhydrous conditions.

The copolymers of the invention can be prepared by bulk polymerization, suspension polymerization, or solution polymerization. The polymerization can be carried out in the presence of an inert normally liquid organic vehicle such as, for example, aromatic hydrocarbons, e.g., benzene, toluene, xylene, ethylbenzene, and the like; oxygenated organic compounds such as anisole, the dimethyl and diethyl esters of ethylene glycol; normally liquid saturated hydrocarbons including open-chain, cyclic and alkyl-substituted-cyclic unsaturated hydrocarbons such as hexane, heptane, cyclohexane, alkylcyclohexanes, decahydronaphthalene and the like.

The polymerization process can be conducted in any convenient manner, e.g., batch, semi-continuous, or continuous processes. The reaction vessel can be any equipment conventionally employed in the production of polymers. The monomeric reactants can be mixed in any order according to conventional polymerization techniques.

Generally, there is always some unreacted monomeric material in the polymerization mass which can be removed by conventional techniques, e.g., heating the polymerization mass under reduced pressure and/or extraction with a solvent which is selective for the unreacted monomer, and/or precipitation of polymer solution in a non-solvent. When the latter two methods are employed, the majority of catalyst can also be removed from the polymerization mass. The typical amount of trace lead (an impurity present in tin) in the final purified polymer mass is below 10 ppm which does not cause any adverse biological response. Although the unreacted monomers can also be removed by heating the polymerization mass under reduced pressure, the catalyst will still remain in the polymerization mass. In this case, it is preferred to use zinc octoate as the catalyst since it is non-toxic and more bio-compatible.

Figure 2:
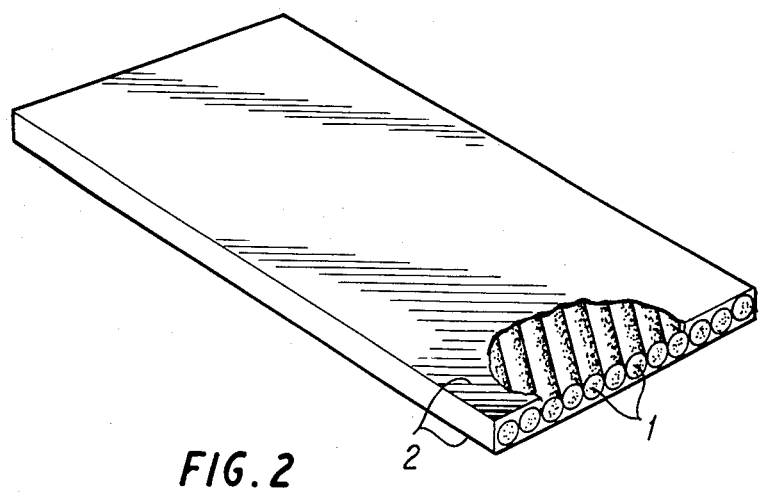
FIG. 2 is a perspective view of a prosthetic tendon or ligament having a plurality of fibers coated with a bioabsorbable polymer.

The copolymers of lactide and epsilon caprolactone of the present invention find utility in the manufacture of films, fibers, moldings and laminates which are prepared by conventional fabricating methods. Of particular note is the use of the present copolymers in the formation of composite articles with carbon fibers for use as body implants. When coated on and/or impregnated into a carbon fiber substrate, the present copolymer, which has good strength and high elongation and is very flexible, provides a protective coating on the carbon fibers which still allows the carbon fiber substrate to have excellent flexibility. This allows easy handling of the coated substrate without fear of the breakage of the carbon fibers. Unlike the prior art materials, the present copolymer affords a composite with carbon fibers which is neither stiff nor in need of a plasticizer. Such an embodiment is illustrated in figure 2, wherein parallel carbon fibers 1 are coated with the polymer of the invention 2. A portion of the polymer has been cut away to observe the fibers. Of course, in preferred embodiments, the actual device may be comprised of many, similar layers, in a single structural article suitable for surgical and medical inplantation.

Where the ultimate implant article is to be utilized for the repair or replacement of damaged tendons, ligaments or other fibrous tissue, the longitudinal axes of the carbon fibers are preferably oriented in substantially the same direction, i.e., parallel to the longitudinal axis of the fibrous tissue to be repaired or replaced in order to promote the proper orientation of the new fibrous tissue growth.

It has been found that completely enveloping the carbon fiber substrate with the copolymer of the present invention effectively prevents the migration of the filamentous carbon after implantation. The bio-absorbable nature of the polymer prevents its interference with the new tissue growth promoting characteristics of the carbon fiber substrate. The polymer functions as a mechanical reinforcer for the carbon fibers during implantation. In the case of fibrous tissue repair, new fibrous tissue grows and orients itself along the longitudinal axes of the carbon fibers. The surgical article may be designed such that the rate of absorption of the bio-absorbable polymer by the body substantially coincides with the rate of new tissue growth, thereby enabling a transference of load from the carbon fiber-polymer composite to the new tissue over extended periods of time. It has been found that this transference of load during tissue growth is essential to the health and stability of the new tissue.

The lactide/epsilon caprolactone polymer of the present invention biodegrades by undergoing hydrolytic de-esterification thus rendering it bio-absorbable. The copolymer of the present invention is a thermoplastic and can be dissolved in many common organic solvents, such as methylenedichloride, toluene, 1,1,1-trichloroethane, chloroform, benzene, dioxane, etc. The lactide/epsilon caprolactone copolymer of the present invention is capable of maintaining its mechanical integrity, in vivo, depending upon its molecular weight, composition, mass and thickness, etc. Likewise, in vitro, the mechanical integrity of the polymer can be maintained by storage under appropriate conditions, e.g., at low temperatures of refrigeration, i.e. 0° C. or below.

Any of the readily available unsized carbon fibers may be employed in the composition, article and method of the invention provided that its tensile strength ranges from about 1.5 to about 2.75 GPa; its tensile modulus ranges from about 100 to about 500 GPa; and its ultimate elongation from about 0.4 to about 3.0%. Carbon fibers having a diameter in the range of from about 5 to about 15 microns, preferably about 10 microns, are satisfactory for preparation of the implant materials. It is particularly preferred to fabricate the implantation composition and articles from continuous tows or bundles containing approximately 10,000 carbon fibers. Generally, the tows or bundles are arranged in any suitable shape or configuration and sprayed, coated or drawn through a solution of the compolymer such that the substrate is completely enveloped by the polymer upon drying.

Depending, of course, upon the ultimate use of the article prepared from the composite, the latter may contain from about 30 to about 95%, preferably about 90%, by weight, of carbon fibers for tendon and ligament replacement. The composite may be considered as a carbon fiber substrate coated with the copolymer or as the copolymer filled with the carbon fibers.

It is essential for the repair or replacement of fibrous tissue that the longitudinal axes of the carbon fibers be oriented in substantially the same direction in order to ensure proper orientation of the new tissue growth upon implantation of the surgical article. For example, it has been found that composites prepared from carbon fibers in mesh or random orientation form, while promoting new tissue growth, gives rise to new tissue which is improperly oriented and, therefore, unstable.

The implant articles may be incorporated in the body of human and non-human animals according to standard and well-known techniques. For example, where the article comprises a replacement tendon or ligament, the article is affixed to the damaged ligament or tendon according to standard procedures. For example, in repairing damaged tendons, the replacement article may be threaded through a drill hole in the appropriate bone and secured to the appropriate area of the tendon to be repaired.

Having generally described this invention, a further understanding can be obtained by reference to certain specific examples which are provided herein for purposes of illustration only and are not intended to be limiting unless otherwise specified.

EXAMPLE I—Preparation of 5/95 L-(−)-lactide/epsilon caprolactone copolymer 7.5 grams of purified, dry L-(−)-lactide melting at 98.3° to 99.3° C. and 142.5 grams of pure epsilon caprolactone distilling at 92° to 94° C./2 mm Hg are placed in a 3-neck glass flask containing a magnetic stirring bar. To the monomeric reactants in the flask is then added 0.0276 grams of pure stannous octoate. The flask and its contents are immersed in an oil heating bath. The contents of the flask are vigorously mixed while a vacuum is applied for about 5 minutes to remove any volatiles. Dry nitrogen is then introduced into the flask to blanket the reactants. The reactants are heated slowly to 140° C. in 2 hours, and then maintained at 140° C. for at least 48 hours.

The flask is removed from the oil heating bath and allowed to cool. To the solid copolymer mass in the flask is then added methylene dichloride. The polymer solution (of about 15% by weight) in methylene dichloride is placed in a large container equipped with a mechanical stirrer. To the vigorously stirred polymer solution is then added 4X isopropyl alcohol to precipitate copolymer. The majority of unreacted monomeric reactants and catalyst are thus removed from the copolymer mass. The copolymer mass can be chopped, in a blender, into fine powder at low temperature. The copolymer powder is then extracted with cold isopropyl alcohol to further remove catalyst and any unreacted monomeric reactants. The copolymer powder is white, elastic and tough after the solvent is evaporated under high vacuum at room temperature. The product is definitely a copolymer since its properties are distinctly different from a mere physical blend of the homopolymers of L-(−)-lactide and epsilon caprolactone. Thermal analysis shows distinctly different differential scanning calorimeter (DSC) curves between the copolymer of L-(−)-lactide and epsilon caprolactone and a polymeric blend of the homopolymers of L-(−)-lactide and epsilon caprolactone. The weight average molecular weight ($\overline{M}_w$) is 419,000 as determined by Gel Permeation Chromatography (GPC). The number average molecular weight ($\overline{M}_w$) is 230,000. DSC of the copolymer reveals a slight amount of crystallinity, with a melting point endo-therm at 54° C. The glass transition temperature ($T_g$) of the copolymer is about −60° C. as determined by thermo-mechanical analysis.

A copolymer film is formed by casting a copolymer solution on a smooth glass surface. After the solvent is removed, the copolymer film is translucent, tough and elastic and has good tensile strength and elongation properties. Physical properties of the copolymer are shown in Table 1.

To investigate the hydrolytic degradability of this copolymer, copolymer films are immersed in a saline solution (0.9% by weight NaCl) at 37° C. The molecular weight changes of the copolymer are analyzed using GPC. The first-order degradation rate constant is determined from a graph of log (molecular weight) versus time, and is also shown in Table 1.

EXAMPLE II—Preparation of 25/75 L-(−)-lactide/epsilon caprolactone copolymer 122 grams of purified, dry L-(−)-lactide melting at 98.3° to 99.3° C. and 366 grams of pure epsilon caprolactone distilled at 92° to 94° C./2 mm Hg are placed in a 3-neck glass flask containing a magnetic stirring bar. To the monomeric reactants in the flask is then added 0.138 grams of pure stannous octoate. The flask and its contents are immersed in an oil heating bath. The contents of the flask are vigorously stirred while a vacuum is applied for about 5 minutes to remove any volatiles. Dry nitrogen is then introduced into the flask to blanket the reactants. The reactants are heated slowly to about 140° C. in 2 hours, and then maintained at 140° C. for 94 hours. The flask is removed from the heat and allowed to cool. To the solid copolymer mass in the flask is then added methylene dichloride. The polymer solution (of about 15% by weight) in methylene dichloride is placed in a large container equipped with a mechanical stirrer. To the vigorously stirred polymer solution is then added 4X isopropyl alcohol to precipitate the copolymer mass. The majority of unreacted monomeric reactants and catalyst are removed from the copolymer mass. The copolymer mass can be chopped, in a blender, into fine powder at low temperature. The copolymer powder is then extracted with cold ispropyl alcohol to further remove catalyst and any unreacted monomeric reactants. The copolymer powder is white, elastic and tough after the solvent is evaporated under high vacuum at room temperature. The product is definitely a copolymer since its properties are distinctly different from a mere physical blend of the homopolymers of L-(−)-lactide and epsilon caprolactone. Thermal analysis shows distinctly different DSC curves between the copolymer and a polymeric blend of the homopolymers of L-(−)-lactide and epsilon caprolactone. The weight average molecular weight ($\overline{M}_w$) of the copolymer is 364,000 as determined by GPC. The number average molecular weight ($\overline{M}_n$) is 172,000. Thermal analysis using DSC and differential thermal analysis (DTA) shows that the copolymer has a glass transition temperature of −32° C. and a melting point of 47° C. The copolymer is formed into a film by casting a copolymer solution on a smooth glass surface. After the solvent is removed, the copolymer film is translucent, tough and elastic. The copolymer has good tensile strength and elongation properties. Physical properties of the copolymer are shown in Table 1.

To investigate the hydrolytic degradability of this copolymer, copolymer films were immersed in a saline solution (0.9% by weight NaCl) at 37° C. The molecular weight changes of the polymer were analyzed using GPC. The first-order degradation rate constant is determined from a graph of log (molecular weight) versus time and is shown in Table 1.

The safety and biocompatibility of this copolymer is demonstrated by the test results shown in Table 2.

EXAMPLE III—Preparation of 30/70 L-(−)-lactide/epsilon caprolactone copolymer

The procedure of Example II is repeated except that 15 grams of L-(−)-lactide, 35 grams of epsilon caprolactone and 0.0105 grams of pure stannous octoate catalyst are blanketed with dry nitrogen in a glass flask and heated for 45 hours at 140° to 142° C. The copolymer is tough and elastic and has good tensile strength and elongation properties. The copolymer has a GPC molecular weight of $\overline{M}_w$=150,000 and $\overline{M}_n$=82,000. DSC of the copolymer reveals a moderate amount of crystallinity with a melting point endotherm of 39° C., and a glass transition temperature of −31° C. Physical properties of the copolymer are shown in Table 1.

EXAMPLE IV—Preparation of 40/60 L-(−)-lactide/epsilon caprolactone copolymer

The procedure of Example II is repeated except that 20 grams of L-(−)-lactide, 30 grams of epsilon caprolactone and 0.0105 grams of pure stannous octoate are placed in a glass flask, blanketed with nitrogen, and heated for 45 hours at 140° to 142° C. The copolymer is tough and elastic and has good tensile strength and elongation properties. The copolymer has a GPC molecular weight of $\overline{M}_w$=323,000 and $\overline{M}_n$=180,000. DSC of the copolymer reveals a moderate amount of crystallinity with a melting point endo-therm of 42° C. and a glass transition temperature of −16° C. Physical properties of the polymer are shown in Table 1.

EXAMPLE V—Use of non-toxic zinc octoate as catalyst for copolymerization

The procedure of Example II is repeated except that 12.5 grams of L-(−)-lactide, 37.5 grams of epsilon caprolactone and 0.0366 grams of pure zinc octoate are placed in a glass flask, blanketed with dry nitrogen and heated for 68 hours at 140° to 145° C. The copolymer is tough and elastic and has good tensile strength of 1190 psi and elongation properties of >2000%. The copolymer has a GPC molecular weight of $\overline{M}_w$=226,000 and $\overline{M}_n$=121,000. DSC of the copolymer reveals a moderate crystallinity with a melting point endotherm of 47° C. and a glass transition temperature of −28° C.

EXAMPLE VI—Preparation of 25/75 D,L-lactide/epsilon caprolactone copolymer.

The procedure of Example II is repeated except that 25 grams of pure D,L-lactide, melting at 128.5° C., 75 grams of epsilon caprolactone and 0.0221 gram of pure stannous octoate are placed in a glass flask, blanketed with dry nitrogen and heated for 78 hours at 145±3° C. The copolymer is tough and elastic and has good tensile strength and elongation properties. The copolymer has a GPC molecular weight of $\overline{M}_w$=307,000 and $\overline{M}_n$=156,000. DSC of the copolymer reveals a slight amount of crystallinity with a melting point endotherm of 39° C. and a glass transition temperature of −30° C. Physical properties are shown in Table 1.

mine the biocompatibility of these implants and their ability to attach to soft tissue.

TABLE 1

Properties of Lactide/Epsilon Caprolactone Copolymers

| Example No. | I | II | III | IV | VI |
|---|---|---|---|---|---|
| Lactide/Epsilon Caprolactone Ratio (w/w) | 5/95[1] | 25/75[1] | 30/70[1] | 40/60[1] | 25/75[2] |
| Ultimate Tensile Strength (ksi) | 7.4 | 1.7 | 3.1 | 1.6 | 1.9 |
| Initial Elastic Modulus (ksi) | 5.1 | 1.1 | 1.8 | 0.7 | 1.6 |
| Elongation to Failure (%) | >2000 | >2000 | >2000 | >2000 | >2000 |
| Hardness (Shore A) | 100 | 84 | 86 | 75 | 78 |
| Specific Gravity | 1.12 | 1.13 | 1.10 | 1.13 | 1.10 |
| Melting Point (°C.) | 54 | 47 | 39 | 42 | 39 |
| Glass Transition Temperature (°C.) | −60 | −32 | −31 | −16 | −30 |
| In Vitro Hydrolytic Degradation Rate Constant (day$^{-1}$) | $1.08 \times 10^{-2}$ | $2.19 \times 10^{-2}$ | $2.26 \times 10^{-2}$ | $3.04 \times 10^{-2}$ | $2.79 \times 10^{-2}$ |

[1] L—(−)-lactide/epsilon caprolactone
[2] D,L—lactide/epsilon caprolactone

EXAMPLE VII—Preparation of coated carbon fiber implants

A 10% (w/v) polymer solution is prepared by dissolving L-(−)-lactide/epsilon caprolactone copolymer, obtained by the procedure according to Example II, in methylene dichloride. A segment of carbon fiber tow containing 10,000 filaments is immersed in the copolymer solution and coated with about 5–8% by weight of copolymer after the solvent is completely evaporated. Since the L-(−)-lactide/epsilon caprolactone copolymer is very flexible and has good strength and an excellent elongation, it provides a good coating protection on carbon fibers and yet still gives the carbon fiber tow excellent flexibility. The copolymer-coated carbon fiber tow can be handled rather easily and can be bent numerous times without breaking up the coating and leaving the carbon fibers unprotected.

In contrast, an L-(−)-polylactide (L-(−)-PLA)-coated carbon fiber tow, prepared in a similar manner, is very stiff causing not only handling difficulties but easy breakage of the carbon fibers every time the carbon fiber tow is bent, because L-(−)-polylactide has no flexibility and does not elongate significantly like the copolymer of the present invention.

An L-(−)-polylactide plasticized with polyethylene glycol (PEG) can only improve its flexibility slightly. However, PEG could reduce interfacial strength between carbon fibers and L-(−)-PLA which causes the L-(−)-PLA coating to detach from the carbon fibers easily under slight shear force.

EXAMPLE VIII—Evaluation of L-(−)-lactide/epsilon caprolactone copolymer-coated carbon fiber ligament implants The evaluation procedure used was identical to that described in Aragona et al, "Soft Tissue Attachment of a Filamentous Carbon-Absorbable Polymer Tendon and Ligament Replacement", *Clinical Orthopaedics and Related Research*, Number 160, October 1981, pages 268–278. L-(−)-lactide/epsilon caprolactone copolymer-coated carbon fiber ligament implants were produced according to the procedure of Example VII. Aside from the polymer coating, these implants are identical to those used in the above-noted reference (Aragona et al). The purpose of this study was to determine the biocompatibility of these implants and their ability to attach to soft tissue.

A 1 cm segment of the Achilles tendon of rabbits was removed, to be replaced by the implant woven through the remnant of the Achilles tendon distally and the musculo-tendonous junction proximally. Ten adult male white New Zealand rabbits were used in this study. The animals were sacrificed in pairs at 1 week, 2 weeks, 4 weeks, 8 weeks and 12 weeks. One animal from each pair was utilized for a histologic study. The other member of each pair was utilized for a mechanical testing study as outlined in the Aragona et al reference, cited above. At sacrifice, 8 of the 10 specimens looked perfect grossly. The other two, a 1-week specimen and a 2-week specimen, showed evidence of infection—probably induced at surgery due to improper sterile technique. However, the 8 successful implants appeared to have rapidly incorporated into the proximal and distal soft tissue anastomoses. The results were virtually identical to those described in Aragona et al.

Mechanical testing was performed as described in the Aragona et al reference. Prior to testing, it was noted that no composite tendons pulled out of their anastomoses and none had ruptured. The rabbits actively used their limbs with full motion early on in the study. The failure strengths obtained from testing are shown superimposed on the results of the Aragona et al reference in the Figure. As can be seen from these results, the regrown structures rapidly gained strength. They approached normal tendon unit strengths sometime between 4 and 8 weeks and retained that strength through 12 weeks. The results are quite similar to those obtained by Aragona et al.

The conclusion from this short evaluation of the implant system is that the present invention, which provides much better handling characteristics for the clinical implant, causes no change in the biological tissue response to the implant or its ability to rapidly incorporate into soft tissue providing rapid soft tissue anastomosis.

TABLE 2

| Biocompatibility Testing | | |
|---|---|---|
| | Test Method | Result |
| (1) | Cytotoxicity (polymer) | Non-toxic |
| (2) | Cytotoxicity (polymer extract) | Non-toxic |
| (3) | Acute Systemic Toxicity | Pass |
| (4) | Intracutaneous Toxicity | Pass |

TABLE 2-continued

| Biocompatibility Testing | | |
|---|---|---|
| | Test Method | Result |
| (5) | Implantation test (Macroscopic Reaction) | Not Significant |
| (6) | Ames Mutagenicity Test | Not-Mutagenic |
| (7) | Trace metals | |
| | Iron | <1.0 ppm |
| | Lead | <1.0 ppm |
| | Tin | 3.0 ppm |

(1) Cytotoxicity (polymer)

A monolayer of L-929 mouse fibroblast cells was grown to confluency and overlaid with Medium 199 supplemented with serum, antibodies, neutral red and agar. The test sample (irregular pieces of polymer-1 cm$^2$) was placed on the solidified overlay surface. Following incubation for 24 hours, the culture was macroscopically examined for evidence of cell decolorization to determine the zone of cell lysis. Any decolorized zone present was examined microscopically to confirm cell lysis.

| Results | | |
|---|---|---|
| Material | Score | Zone of lysis (mm) |
| Polymer | N | — |
| Negative Control (U.S.P. Negative Control Plastic) | N | — |
| Positive Control (latex) | T | 6 |

N(non-toxic) - No change in cell morphology in proximity to test sample.
T(toxic) - Death and/or degeneration of cells directly beneath the area of test sample and possibly also with a zone extended beyond the test sample. Where a zone of lysis was observed, the distance from the edge of the sample to the edge of the zone was measured and reported in millimeters (mm).

(2) Cytotoxicity (polymer extract)

A monolayer of L-929 mouse fibroblast cells was grown to confluency and overlaid with Medium 199 supplemented with serum, antibiotics, neutral red and agar. The test sample (a filter disc to which 0.1 ml of an extract was applied, the extract being prepared by extracting 4 grams of polymer with 20 ml of saline for 24 hours at 70° C.) was placed on the solidified overlay surface. Following incubation for 24 hours, the culture was macroscopically examined for evidence of cell decolorization to determine the zone of cell lysis. Any decolorized zone present was examined microscopically to confirm cell lysis

| Results | | |
|---|---|---|
| Material | Score | Zone of lysis (mm) |
| Polymer | N | — |
| Negative Control (U.S.P. Negative Control Plastic) | N | — |
| Positive Control (latex) | T | 6 |

N(non-toxic) - No change in cell morphology in proximity to test sample.
T(toxic) - Death and/or degeneration of cells directly beneath the area of test sample and possibly also with a zone extended beyond the test sample. Where a zone of lysis was observed, the distance from the edge of the sample to the edge of the zone was measured and reported in millimeters (mm).

(3) Acute Systemic Toxicity

Healthy, young white mice ranging in body weight from 17 to 23 grams were used as test animals. The animals were housed in stock cages and offered food and water ad libitum.

Two groups, each consisting of five mice, were used for each extract. The extract was prepared by extracting 4 grams of the polymer with 20 ml of the appropriate extractant for 72 hours at 50° C. One group was injected with the extract of the Test Material, while the other group was injected with the Blank. After injection, the animals were observed immediately and at 4, 24, 48 and 72 hours. Initial and final body weights were recorded as well as mortality and/or reactions. If, during the observation period, none of the animals treated with the extract of the Test Material show a significantly greater reaction than the animals treated with the Blank, the material meets the requirements of the test.

| | Results Mortality and Body Weight Data | | | | | | | |
|---|---|---|---|---|---|---|---|---|
| | TEST MATERIAL | | | | BLANK | | | |
| Extract, Dose and Route | Animal Number | Weight (gms) Day 0 | (gms) Day 3 | #Dead #Tested | Animal Number | Weight (gms) Day 0 | (gms) Day 3 | #Dead #Tested |
| Sodium Chloride Injection (I.V. 50 ml/Kg) | 1 | 23 | 25 | 0/5 | 1 | 18 | 21 | 0/5 |
| | 2 | 22 | 25 | | 2 | 21 | 24 | |
| | 3 | 23 | 25 | | 3 | 18 | 21 | |
| | 4 | 20 | 21 | | 4 | 18 | 22 | |
| | 5 | 23 | 25 | | 5 | 18 | 21 | |
| Ethanol in Sodium Chloride Injection (1:20) (I.V. 50 ml/Kg) | 1 | 22 | 23 | 0/5 | 1 | 18 | 19 | 0/5 |
| | 2 | 21 | 23 | | 2 | 18 | 21 | |
| | 3 | 22 | 24 | | 3 | 19 | 23 | |
| | 4 | 20 | 25 | | 4 | 20 | 22 | |
| | 5 | 22 | 25 | | 5 | 18 | 19 | |
| Polyethylene Glycol 400 (I.P. 10 g/Kg) | 1 | 23 | 26 | 0/5 | 1 | 17 | 18 | 0/5 |
| | 2 | 22 | 22 | | 2 | 21 | 25 | |
| | 3 | 21 | 23 | | 3 | 19 | 22 | |
| | 4 | 22 | 23 | | 4 | 17 | 21 | |
| | 5 | 22 | 24 | | 5 | 21 | 24 | |
| Cottonseed Oil (I.P. 50 ml/Kg) | 1 | 22 | 24 | 0/5 | 1 | 23 | 26 | 0/5 |
| | 2 | 22 | 25 | | 2 | 22 | 24 | |
| | 3 | 23 | 23 | | 3 | 21 | 23 | |
| | 4 | 21 | 22 | | 4 | 21 | 21 | |
| | 5 | 22 | 23 | | 5 | 22 | 23 | |

(4) Intracutaneous Toxicity

Two healthy, previously unused New Zealand rabbits were used as test animals for each extract. The extract was prepared by extracting 4 grams of the polymer with 20 ml of the appropriate extractant for 72 hours at 50° C. Animals were housed individually and allowed food and water ad libitum. Prior to injection, the hair was closely clipped from the back and flanks of each rabbit. Exactly 0.2 ml of the extract of the Test Material was injected intracutaneously into ten separate sites on the right side of the back of each animal while 0.2 ml of the extracting medium (Blank) was injected into five separate sites on the left side. Injection sites were examined 24, 48 and 72 hours after injection for erythema and edema. The average tissue reaction to the extract of the Test Material was compared with the Blank. The requirements of the test were met if no significant differences were noted.

Results

| Extract | | Rabbit No. | 24 HR. ER | 24 HR. ED | 48 HR. ER | 48 HR. ED | 72 HR. ER | 72 HR. ED |
|---|---|---|---|---|---|---|---|---|
| Sodium | Test | 8093 | 0 | 0 | 0 | 0 | 0 | 0 |
| Chloride | Blank | | 0 | 0 | 0 | 0 | 0 | 0 |
| (SC) | Test | 8103 | 0 | 0 | 0 | 0 | 0 | 0 |
| | Blank | | 0 | 0 | 0 | 0 | 0 | 0 |
| Alcohol in | Test | 8105 | 0 | 0 | 0 | 0 | 0 | 0 |
| Sodium | Blank | | 0 | 0 | 0 | 0 | 0 | 0 |
| Chloride | Test | 8106 | 0 | 0 | 0 | 0 | 0 | 0 |
| (1:20) | Blank | | 0 | 0 | 0 | 0 | 0 | 0 |
| (AS) | | | | | | | | |
| Polyethylene | Test | 8107 | 0 | 0 | 2 | 1 | 1 | 1 |
| Glycol | Blank | | 0 | 0 | 2 | 1 | 1 | 1 |
| 400 | Test | 8108 | 3 | 2 | 2 | 1 | 2 | 1 |
| (PEG) | Blank | | 2 | 2 | 2 | 1 | 2 | 1 |
| Cottonseed | Test | 8109 | 1 | 2 | 0 | 1 | 0 | 1 |
| Oil | Blank | | 1 | 2 | 0 | 1 | 0 | 1 |
| (CSO) | Test | 8110 | 0 | 1 | 0 | 1 | 0 | 1 |
| | Blank | | 0 | 1 | 0 | 1 | 0 | 1 |

ER = Erythema
0 = None
1 = Barely Perceptible
2 = Well Defined
3 = Moderate
4 = Severe ED = Edema
0 = None
1 = Barely Perceptible
2 = Well Defined
3 = Raised 1 mm
4 = Raiseed > 1 mm $\bar{X}$ Test − $\bar{X}$ Blank =     Pass
SC   0.0−0.0 =   0.0   X
AS   0.0−0.0 =   0.0   X
PEG  1.3−1.3 =   0.0   X
CSO  0.7−0.7 =   0.0   X

(5) Implantation Test (Macroscopic Reaction)

Two healthy, adult New Zealand white rabbits weighing in excess of 2.5 Kg. were used as test animals. The rabbits were housed individually and allowed food and water ad libitum. Prior to the implantation, the back of each animal was clipped on both sides of the spinal column. All loose hair was removed after clipping and prior to implantation to prevent entry into the implantation site.

Four strips of steam sterilized test material, approximately 1 mm wide and 10 mm long were introduced into the right paravertebral muscle of each rabbit. Two strips of U.S.P. negative control plastic were implanted in the left paravertebral muscle of each rabbit.

The animals were sacrificed 5 days after implantation and the entire paravertebral muscle on each side of the spinal cord removed. Cross sections of the muscles were made to locate the implants. The tissue surrounding the center portion of each implant was examined macroscopically.

Results

| Rabbit | Sample | Test | Control |
|---|---|---|---|
| 7932 | 1 | 1 | 1 |
| | 2 | 1 | 1 |
| | 3 | 1 | 1 |
| | 4 | 1 | 1 |
| | 5 | 1 | 1 |
| 7935 | 1 | 1 | 0 |
| | 2 | 1 | 1 |
| | 3 | 1 | 1 |
| | 4 | 1 | 1 |
| | 5 | 1 | 1 |
| Mean ($\bar{X}$) | | 1.0 | 0.9 |

Scoring Key

| Score | Capsule Formation |
|---|---|
| 0 | None Noted |
| 1 | Up to 0.5 mm |
| 2 | 0.5 to 1.0 mm |
| 3 | 1.0 to 2.0 mm |
| 4 | >2.0 mm |

Reaction Index
$\bar{X}$ (Test) − $\bar{X}$ (Control) = 0.1

| 0−0.5 | Not Significant |
| 0.6−1.0 | Trace |
| 1.1−2.0 | Slight |
| 2.1−3.0 | Moderate |
| >3.1 | Marked |

(6) Ames Mutagenicity Test

A Salmonella/mammalian mutagenicity test was performed to determine if a saline extract of the polymer would cause mutagenic changes in histidine dependent mutant strains of *Salmonella typhimurium*. The method of Ames et al as reported in *Methods for Detecting Carcinogens and Mutagens with the Salmonella/Mammalian Mutagenicity Test* (1975) was employed.

Test sample—a polymer, saline (0.85%) extract was prepared by adding 4 grams of sample to 20 ml of saline and autoclaving at 121° C. for one hour.

Bacterial test strains—four strains of specially constructed histidine mutants of *Salmonella typhimurium*, TA 98, TA 100, TA 1535 and TA 1537, developed by Dr. B. Ames, University of California, Berkeley were employed.

Activation system—S-9 Activation Mix is composed mainly of the microsomal fraction from a rat liver homogenate. The S-9 mix was used for the detection of mutagenic properties that require metabolic biotransformation to their active mutagenic form. S-9 mix employed was Aroclor 1254—induced (Litton Bionetics, Inc., Kensington, Md., Lot #REL 091).

Negative controls—the solvent elution vehicle was test with each bacterial strain to determine the number of spontaneous revertant colonies for each test population. These data represent a base rate to which the number of revertant colonies developed in each test sample plate were compared to determine whether the test sample had significant mutagenic properties. Mutagenesis of the test sample is demonstrated by at least a two-fold increase of test sample revertant colonies compared to spontaneous revertant colonies for the tester strain.

Positive controls—known mutagens, Dexon and methylene dianiline (MDA), were used as positive controls to demonstrate that each test strain was sensitive to histidine mutation (producing at least a two-fold increase over the spontaneous reversion rate). MDA requires metabolic activation to induce mutagenic results;

therefore, it was tested (on strain TA 100 only) with and without S-9 mix to verify the bioactivation properties of the S-9 rat liver preparation.

Preliminary toxicity screen—the sample extract was first evaluated by a spot plate technique modeled after the antimicrobial zone of inhibition test. This assay determines whether the sample concentration is toxic to the test strains. Inhibition of bacterial growth by toxic solution interfers with the Ames plate incorporation assay. No significant inhibition was caused by the saline extract of the sample tested.

Ames plate incorporation assay—the principle technique of the Ames test consists of a plate incorporation assay from which direct revertant colony counts are obtained from the test plates. Minimal nutrient agar plates are seeded with both a tester strain population and the test solution suspended together in a semi-solid overlay. Test plates are prepared providing for either the presence or absence of S-9 activation mix supplemented in the overlay. Following a 48 hour incubation period at 30° C., the number of colonies in each test plate are recorded as revertant colonies for comparison with spontaneous revertant rates for each strain.

| Eluates | Results Salmonella typhiumurium Tester Strains | | | |
|---|---|---|---|---|
| | TA98 | TA100 | TA1535 | TA1537 |
| Spot Plate Inhibition | Zone of Inhibition (mm) | | | |
| Saline (− control) | 0 | 0 | 0 | 0 |
| Saline extract | 0 | 0 | 0 | 0 |
| Plate Incorporation Assay | Number of Revertant Colonies (Average of Duplicate Plates) | | | |
| Saline (− control) | 17.0 | 57.5 | 6.0 | 4.5 |
| Saline extract | 13.5 | 55.0 | 7.0 | 4.0 |
| Saline w/S-9 (− control) | 17.5 | 60.5 | 12.0 | 7.0 |
| Saline w/S-9 extract | 22.0 | 58.0 | 8.5 | 6.5 |
| Dexon (+ control) | 422.0 | 377.0 | 28.0 | 216.0 |
| Dexon w/S-9 | 430.0 | 388.5 | 26.5 | 230.0 |
| MDA (+ control) | | 73.0 | | |
| MDA w/S-9 (+ control) | | 223.0 | | |

In no case was there a two-fold increase in the reversion rate of the test strains in the presence of a saline extract of the test material.

(7) Trace metals

A 4.09 gram portion of the polymer was wetted with concentrated $H_2SO_4$, charred, and then ashed at 550° C. The residue was diluted to 12.0 ml with 2% $HNO_3$ and elements of interest were determined by atomic absorption spectrophotometry.

Results

Iron—less than 1.0 ppm in original sample
Lead—less than 1.0 ppm in original sample.
Tin—3.8 ppm in original sample.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A bio-absorbable copolymer consisting essentially of lactide and epsilon caprolactone, wherein said epsilon caprolactone is present in amounts of 60-95% by weight and said lactide is present in amounts of 5-40% by weight, and wherein said copolymer is tough, elastic, has good tensile strength and elongation to failure in excess of 2000%, and is non-brittle and non-rigid.

2. The bio-absorbable copolymer according to claim 1 wherein said lactide is optically active or optically inactive.

3. The bio-absorbable copolymer according to claim 2, wherein the optically active lactide is L-(−)-lactide having a melting point of about 95°-98° C.

4. The bio-absorbable copolymer according to claim 2, wherein the optically inactive lactide is D,L-lactide having a melting point of about 115°-129° C.

5. The bio-absorbable copolymer according to claim 1, wherein said polymer comprises about 75% by weight of epsilon caprolactone and about 25% by weight of lactide.

6. A bio-compatible composition suitable for fabricating a surgical article for the repair or replacement of a part of the body of a human or animal comprising a composite of a bio-absorbable copolymer of lactide and epsilon caprolactone, wherein epsilon caprolactone is present in amounts of 60-95% by weight and said lactide is present in amounts of 5-40% by weight, and wherein said copolymer is tough, elastic, has good tensile strength and elongation to failure in excess of 2000% and is non-brittle and non-rigid, and at least one substrate of a plurality of carbon fibers, said fibers having a longitudinal axis.

7. The composition according to claim 6, wherein said copolymer of lactide and epsilon caprolactone comprises about 75% by weight of epsilon caprolactone and about 25% by weight of lactide.

8. The composition according to claim 6, wherein the longitudinal axes of the carbon fibers in each at least one substrate are oriented in substantially the same direction.

9. The composition according to claim 6, wherein each of said carbon fibers has a diameter in the range of from about 5 to about 15 microns.

10. The composition according to claim 9, wherein each of said carbon fibers has a diameter of about 10 microns.

11. The composition according to claim 6, wherein said composite contains from about 30 to about 95%, by weight, of carbon fibers.

12. The composition according to claim 11, wherein said composite contains about 90% by weight, of carbon fibers.

13. The composition according to claim 6, wherein said composite comprises said at least one substrate of carbon fibers coated with said bio-absorbable copolymer of lactide and epsilon caprolactone.

14. The composition according to claim 6, wherein said composite comprises said bio-absorbable copolymer of lactide and epsilon caprolactone filled with said at least one substrate of carbon fibers.

15. The composition according to claim 6, wherein said substrate comprises a substantially uniplanar layer of carbon fibers.

16. A bio-compatible surgical article, having a longitudinal axis, for the repair or replacement of a tendon or ligament comprising at least one substrate of a plurality of carbon fibers coated with a bio-absorbable copolymer of lactide and epsilon caprolactone, wherein said epsilon caprolactone is present in amounts of 60-95% by weight and said lactide is present in amounts of 5-40% by weight, and wherein said copolymer is tough, elastic, has good tensile strength and elongation to failure in excess of 2000% and is non-brittle and non-rigid, and said carbon fibers are oriented substantially parallel to each other and to said longitudinal axis.

17. The surgical article according to claim 16 wherein said copolymer of lactide and epsilon caprolactone comprises about 75% by weight of epsilon caprolactone and about 25% by weight of lactide.

18. The surgical article according to claim 16, wherein each of said carbon fibers has a diameter in the range of from about 5 to about 15 microns.

19. The surgical article according to claim 18, wherein each of said carbon fibers has a diameter of about 10 microns.

20. The surgical article according to claim 16, wherein said article comprises from about 30 to about 95% by weight, of said carbon fibers.

21. The surgical article according to claim 20, wherein said article comprises about 90% by weight of said carbon fibers.

22. A method for repairing a damaged ligament comprising overlaying the damaged part of said ligament with a bio-compatible surgical article, having a longitudinal axis, comprising at least one substrate of a plurality of carbon fibers, having a longitudinal axis, coated with a bio-absorbable copolymer of lactide and epsilon caprolactone, and said epsilon caprolactone is present in amounts of 60-95% by weight and said lactide is present in amounts of 5-40% by weight, and wherein said copolymer is tough, elastic, has good tensile strength and elongation to failure in excess of 2000% and is non-brittle and non-rigid such that a longitudinal axes of the carbon fibers are substantially parallel to the longitudinal axes of the fibrous tissue of said ligament and securing said surgical article to said ligament or tissue connective therewith at sites on opposite sides of said damaged portions thereof.

23. A method for repairing a damaged tendon comprising overlaying the damaged part of said tendon with a bio-compatible surgical article, having a longitudinal axis, comprising at least one substrate of a plurality of carbon fibers, having a longitudinal axis, coated with a bioabsorbable copolymer of lactide and epsilon caprolactone, and said epsilon caprolactone is present in amounts of 60-95% by weight and said lactide is present in amounts of 5-40% by weight, and wherein said copolymer is tough, elastic, has good tensile strength and elongation to failure in excess of 2000% and is non-brittle and non-rigid such that a longitudinal axes of the carbon fibers are substantially parallel to the longitudinal axes of the fibrous tissue of said tendon and securing said surgical article to said tendon or tissue connective therewith at sites on opposite sides of said damaged portions thereof.

* * * * *